US010433832B2

(12) United States Patent
Hasan et al.

(10) Patent No.: US 10,433,832 B2
(45) Date of Patent: Oct. 8, 2019

(54) LAPAROSCOPIC SUTURE DEVICE WITH IMPULSE DEPLOYMENT

(71) Applicant: Surgimatix, Inc., Elk Grove Village, IL (US)

(72) Inventors: Jafar S. Hasan, Oak Brook, IL (US);
Wai N. Chin, Glenview, IL (US);
James Orrico, Chicago, IL (US);
Adam A. Saban, Lockport, IL (US);
Gary M. Kobylewski, Hoffman Estates, IL (US)

(73) Assignee: Surgimatix, Inc., Hillside, IL (US)

( * ) Notice: Subject to any disclaimer, the term of this patent is extended or adjusted under 35 U.S.C. 154(b) by 775 days.

(21) Appl. No.: 14/988,436

(22) PCT Filed: Dec. 30, 2015

(86) PCT No.: PCT/US2015/068025
§ 371 (c)(1),
(2) Date: Jan. 5, 2016

(87) PCT Pub. No.: WO2016/109644
PCT Pub. Date: Jul. 7, 2016

(65) Prior Publication Data
US 2017/0290581 A1    Oct. 12, 2017

Related U.S. Application Data

(60) Provisional application No. 62/097,882, filed on Dec. 30, 2014.

(51) Int. Cl.
*A61B 17/04* (2006.01)
*A61B 17/062* (2006.01)
*A61B 17/06* (2006.01)

(52) U.S. Cl.
CPC ...... *A61B 17/0469* (2013.01); *A61B 17/0485* (2013.01); *A61B 17/0625* (2013.01);
(Continued)

(58) Field of Classification Search
CPC ......... A61B 17/0469–049; A61B 2017/06014; A61B 2017/0608; A61B 2017/06076; A61B 2017/922–928; A61B 2017/07285
See application file for complete search history.

(56) References Cited

U.S. PATENT DOCUMENTS 5,364,408 A * 11/1994 Gordon .............. A61B 17/0469
112/169
5,931,844 A * 8/1999 Thompson ......... A61B 17/0487
606/139

(Continued)

OTHER PUBLICATIONS

International Search Report Application No. PCT/US2015/068025 reported dated May 4, 2016.

*Primary Examiner* — Ryan J. Severson
*Assistant Examiner* — Charles M Wei
(74) *Attorney, Agent, or Firm* — Miller, Matthias & Hull LLP

(57) ABSTRACT

A suturing device is provided. The suturing device may include at least one suturing needle, a drive mechanism and an impulse mechanism. The drive mechanism may be operatively coupled to the suturing needle and configured to advance the suturing needle from a retracted position to an extended position during engagement, and retract the suturing needle from the extended position to the retracted position during disengagement. The impulse mechanism may be operatively coupled to the drive mechanism and configured to accumulate energy during engagement of the suturing needle, and instantaneously release the accumulated energy through the drive mechanism during disengagement.

22 Claims, 15 Drawing Sheets

(52) U.S. Cl.
CPC . *A61B 17/06004* (2013.01); *A61B 2017/0608* (2013.01); *A61B 2017/06042* (2013.01); *A61B 2017/06076* (2013.01)

(56) References Cited

U.S. PATENT DOCUMENTS

| | | | |
|---|---|---|---|
| 8,202,290 B2* | 6/2012 | Smith | A61B 17/32093 |
| | | | 606/185 |
| 9,867,609 B2* | 1/2018 | Chin | A61B 17/0482 |
| 9,936,942 B2* | 4/2018 | Chin | A61B 17/0469 |
| 2008/0132919 A1 | 6/2008 | Chui et al. | |
| 2009/0093824 A1* | 4/2009 | Hasan | A61B 17/0401 |
| | | | 606/139 |
| 2010/0152751 A1 | 6/2010 | Meade et al. | |
| 2012/0165838 A1* | 6/2012 | Kobylewski | A61B 17/0469 |
| | | | 606/144 |
| 2014/0171976 A1 | 6/2014 | Martin et al. | |
| 2014/0236193 A1* | 8/2014 | Chin | A61B 17/0401 |
| | | | 606/145 |
| 2015/0090271 A1* | 4/2015 | Cruzada | A61F 6/005 |
| | | | 128/831 |

\* cited by examiner

LAPAROSCOPIC SUTURE DEVICE WITH IMPULSE DEPLOYMENT

CROSS-REFERENCE TO RELATED APPLICATION

This application is based on and claims priority to International Application Serial No. PCT/US15/68025, filed on Dec. 30, 2015, which claims priority to U.S. Provisional Application No. 62/097,882 filed on Dec. 30, 2014.

FIELD OF THE DISCLOSURE

The present disclosure generally relates to medical fastening devices, and more particularly, relates to sutures and suturing devices for fastening tissue and/or prosthetic material.

BACKGROUND OF THE DISCLOSURE

The fastening of tissues has long been a need in the medical industry, and correspondingly, a finite number of fastening devices have been developed for different applications and uses. Among these devices are laparoscopic fastening devices or tackers which are often used with minimally invasive procedures such as laparoscopic repair of hernias, and the like. A typical laparoscopic procedure involves the insertion of thin, elongated instruments into relatively small incisions or access ports in the abdomen to access hernia defects in the abdominal wall from the inside. Moreover, the laparoscopic instruments are used to position a prosthetic mesh over the defect and fasten the prosthetic mesh against the inner abdominal wall using tacks, or the like.

Conventional laparoscopic tackers provide a relatively thin and elongated tubular member containing deployable tacks and having an end-firing mechanism positioned at the distal tip thereof. In particular, the end-firing mechanism is configured to deploy tacks directly from the tip of the elongated member in an axial manner, and thus, ideal application suggests positioning the elongated member perpendicularly against the tissue surface to be tacked. However, due to several factors, such as the relatively rigid and elongated nature of the laparoscopic tacker, the limited locations and number of access ports available, and the typical location of hernia defects, it is difficult to position the end of the laparoscopic device squarely against the inner wall of the abdomen. In practice, a surgeon using a laparoscopic tacker typically positions the tacker with one hand, sometimes even slightly bending the instrument while using his other hand to press against the outer wall of the abdomen, in order to achieve the best possible angle for installing the tacks.

Due to the limited access to hernia defects and the minimally invasive nature of typical hernia repairs, laparoscopic tackers tend to use simple-action type mechanisms to deploy tacks, and correspondingly, employ tacks with basic means for fastening prosthetic mesh to the inner abdominal wall. More specifically, conventional tackers employ screw-type or simple push-type actions to install tacks with threads or barbs which help embed the tacks within abdominal tissue. Over time, especially in the case of metal, coil-shaped tacks, these tacks may cause irritation or pain to the patient, become dislodged from the abdominal wall, or cause other complications post-surgery. To address such drawbacks associated with metal tacks, absorbable tacks have been developed and employed. Absorbable tacks are designed to be eventually absorbed by the body, and thus, cause less irritation or pain to the patient over time. However, absorbable tacks also tend to provide holding or tensile strength that is less than optimal.

Another problem encountered by surgeons while using conventional laparoscopic devices is the difficulty with which to finally deploy a given fastener into the desired region of tissue. More specifically, a successful fastening or suturing process requires not only proper insertion of the fastener into tissue, but also proper release of the fastener from the fastening device and into the tissue. Due to the tough and/or fibrous nature of some types of tissue, it may be physically challenging to quickly and neatly release a fastener into the tissue while operating the fastening device by hand. To address this issue, some devices offer convenience features such as fully automated and/or simple-action mechanisms which insert as well as release the fastener in a single action. While such convenience features may facilitate fastener installation, these features also compromise the degree of control the surgeon has over the installation process. In particular, these convenience features tend to perform both the insertion and the release actions too quickly, suddenly and/or discretely, thereby limiting tactile feedback to the surgeon and resulting in an undesirable disconnect from the fastening process. Also, depending on the force or speed with which such convenience features insert or release fasteners, there is a potential for tissue trauma or bleeding.

Accordingly, there is a need for minimally invasive or laparoscopic means of fastening tissue which provides a more effective and reliable means for closing tissue and/or fastening prosthetic mesh to tissue. There is also a need for a medical fastening or suturing device which employs fasteners or sutures that reduce irritation, pain, and other complications to the patient without adversely affecting holding strength. Furthermore, there is a need for a medical fastening or suturing device which not only facilitates the insertion, release and deployment of fasteners or sutures into tissue, but also provides the surgeon with sufficient control throughout the process.

SUMMARY OF THE DISCLOSURE

In accordance with one aspect of the disclosure, a suturing device is provided. The suturing device includes at least one suturing needle, a drive mechanism and an impulse mechanism. The drive mechanism may be operatively coupled to the suturing needle and configured to advance the suturing needle from a retracted position to an extended position during engagement, and retract the suturing needle from the extended position to the retracted position during disengagement. The impulse mechanism may be operatively coupled to the drive mechanism and configured to accumulate energy during engagement of the suturing needle, and instantaneously release the accumulated energy through the drive mechanism.

In accordance with another aspect of the disclosure, a suturing device is provided. The suturing device may include an elongate member extending between a working end and a control end, a drive mechanism and an impulse mechanism. The working end of the elongate member may have a distal needle and a proximal needle disposed therein. The drive mechanism may be disposed within the elongate member and operatively coupled to each of the distal and proximal needles. The drive mechanism may be configured to advance each of the distal and proximal needles from a retracted position to an extended position during engagement, and retract each of the distal and proximal needles from the extended position to the retracted position during disengagement. The impulse mechanism may be disposed within the control end and operatively coupled to the drive mechanism in a manner configured to selectively engage and disengage each of the distal and proximal needles. The impulse mechanism may have at least a trigger, a tensioning device and a ratchet arrangement configured to accumulate energy during engagement, and instantaneously release the accumulated energy through the drive mechanism.

In accordance with yet another aspect of the disclosure, a suturing device is provided. The suturing device may include an elongate member, a drive mechanism and an impulse mechanism. The elongate member may extend between a working end and a control end and have a track for receiving one or more deployable sutures therein. The working end may have a firing aperture disposed in communication with the track and a distal needle and a proximal needle rotatably disposed therein. The drive mechanism may be disposed within the elongate member and include at least a distal drive link operatively coupled to the distal needle and a proximal drive link operatively coupled to the proximal needle. The drive mechanism may be configured to advance each of the distal and proximal needles from a retracted position to an extended position during engagement, and retract each of the distal and proximal needles from the extended position to the retracted position during disengagement. The impulse mechanism may be disposed within the control end and operatively coupled to the drive mechanism. The impulse mechanism may have at least a trigger, a tensioning device, a ratchet latch and a ratchet pawl configured to couple the trigger to the drive mechanism and accumulate energy in the tensioning device during engagement, and decouple the trigger from the drive mechanism and instantaneously release the accumulated energy through the drive mechanism.

These and other aspects and features of the disclosure will be better understood upon reading the following detailed description when taken into conjunction with the accompanying drawings.

Figure 1:
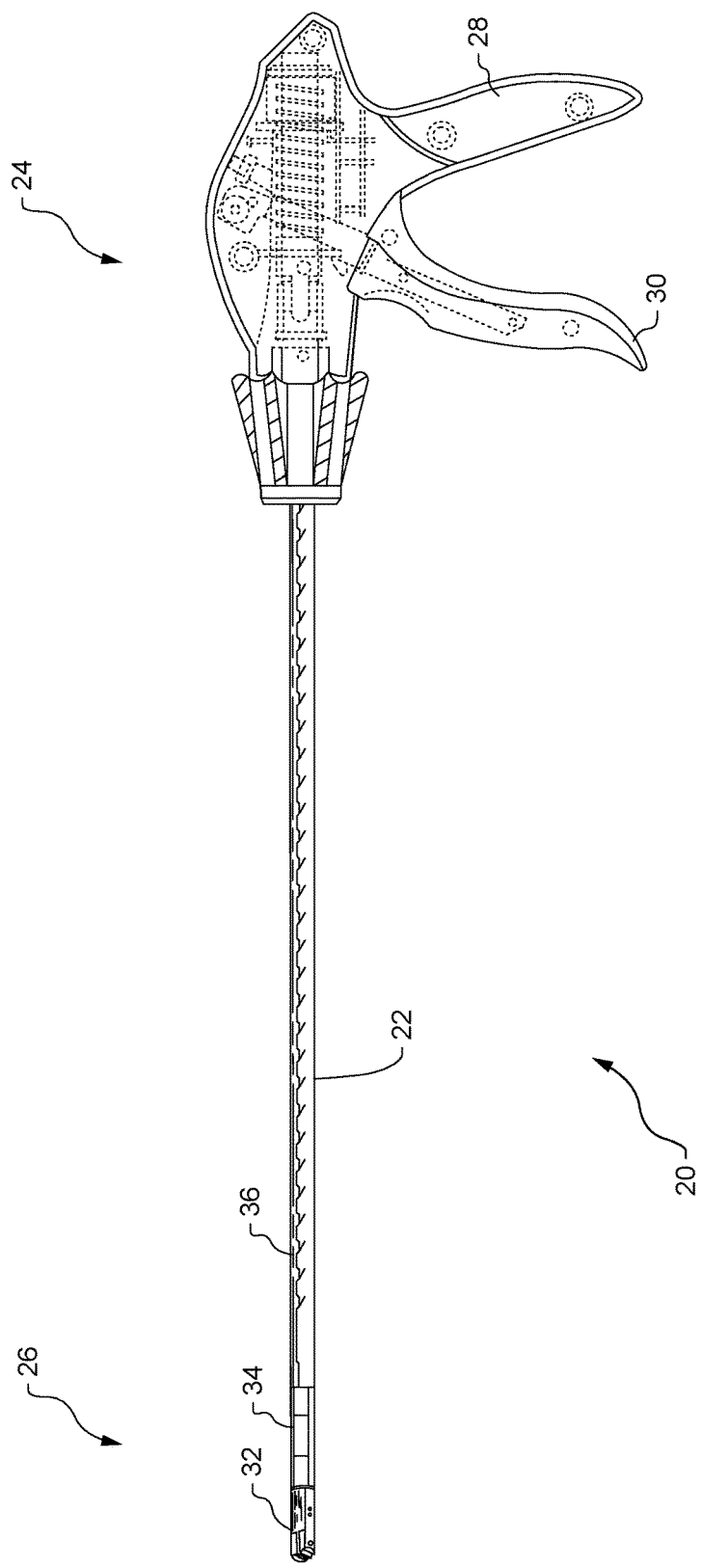
FIG. 1 is a perspective view of a suturing device constructed in accordance with the teachings of the present disclosure.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions and equivalents falling within the spirit and scope of the present disclosure.

DETAILED DESCRIPTION

Referring now to the drawings, and with specific reference to FIG. 1, a medical fastening or suturing device constructed in accordance with the teachings of the present disclosure is generally referred to by reference numeral 20. The suturing device 20, as will be described in further detail herein, may advantageously enable convenient yet effective means of providing fasteners within a surgical environment. The disclosed embodiments may additionally facilitate the installation and deployment of fasteners or sutures during minimally invasive surgical procedures, such as laparoscopic procedures, and the like, without compromising control over the installation and deployment processes. As used for laparoscopic treatment of a hernia, the embodiment of FIG. 1, for example, may be employed to reach beneath sections of tissue, within or around the abdominal region, to fasten tissues of the abdominal wall or to fasten prosthetic mesh to the abdominal wall from the inside. Although the embodiments disclosed herein demonstrate tissue fastening as applied to laparoscopic applications, it will be understood that the present disclosure may be equally or similarly applied to other medical procedures.

As shown in FIG. 1, the suturing device 20 may generally include an elongate member 22 which extends between a control end 24 disposed at a proximal end thereof, and a working end 26 disposed at a distal end thereof. The control end 24 may generally include a grip 28 as well as a trigger 30, or any other suitable means for receiving input or triggering actions from a user and converting the input or actions into a suturing action that is performed at the working end 26 of the suturing device 20. The working end 26 may generally be configured with a firing aperture 32, or a fastening interface disposed at a longitudinal side thereof, through which fasteners or sutures 34 may be deployed or installed in tissue and/or prosthetic material. Furthermore, one or more of the sutures 34 to be deployed may be provided along the elongate member 22 and distally advanced or fed toward the firing aperture 32 of the working end 26, for example, along one or more guides or tracks 36 longitudinally disposed within the elongate member 22.

Figure 2:
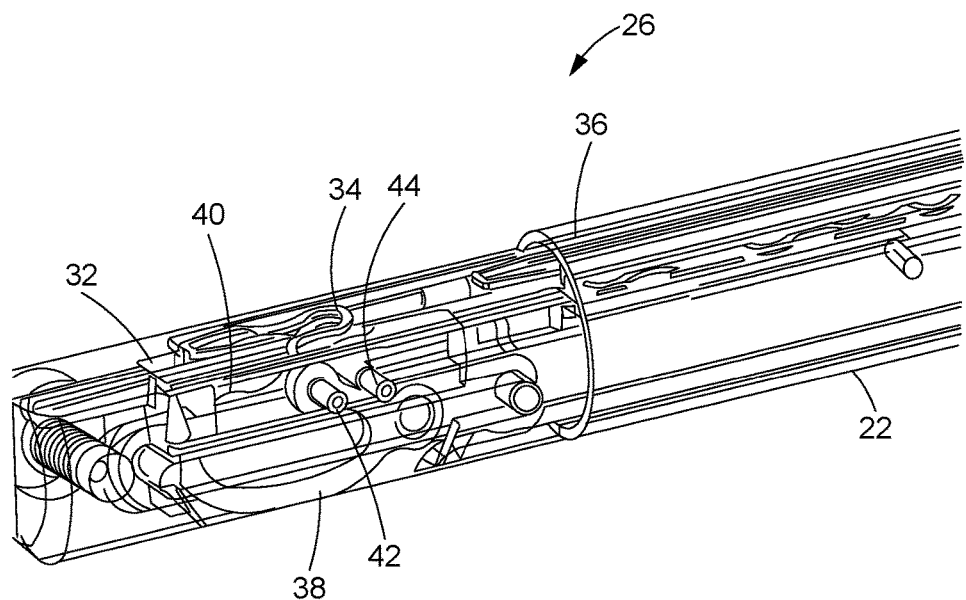
FIG. 2 is a partial perspective view of the working end of a suturing device with fully retracted first and second needles.
Figure 3:
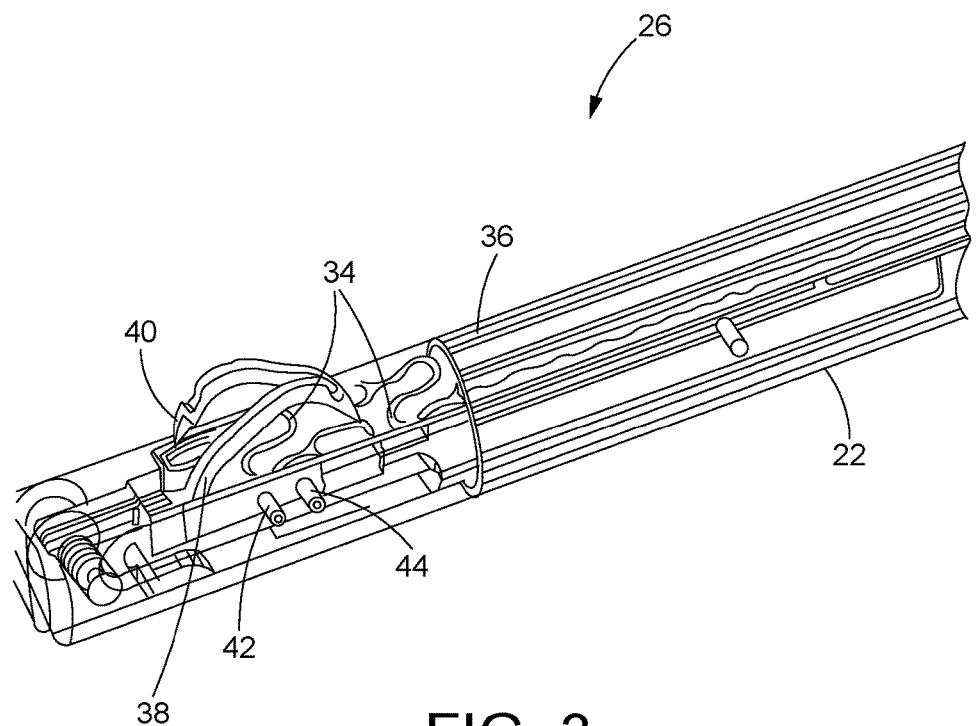
FIG. 3 is a partial perspective view of the working end of a suturing device with partially extended first and second needles.

As shown in more detail in FIGS. 2 and 3, the working end 26 of the suturing device 20 of FIG. 1 may at least partially enclose a first needle 38 and a second needle 40, each of which may be substantially concealed within the firing aperture 32 of the working end 26 in a default or fully retracted position. More specifically, the first needle 38 may be rotatably and pivotally disposed about a first fixed axis 42, and the second needle 40 may be rotatably and pivotally disposed about a second fixed axis 44. Moreover, the first axis 42 may be axially offset but substantially parallel to the second axis 44, for example, such that the first needle 38 is distally positioned relative to the suturing device 20 and the second needle 40 is proximally positioned relative to the suturing device 20. In other alternative embodiments, each of the first and second needles 38, 40 may be coaxially disposed about a common axis. In still further embodiments, a single needle or more than two needles may be disposed within the firing aperture 32 and comprise any one of a plurality of different arrangements.

Still referring to FIGS. 2 and 3, each of the first and second needles 38, 40 may be configured to rotate in opposing directions between respective retracted and extended positions. For example, during advancement, the first or distal needle 38 may be configured to proximally rotate toward the elongate member 22, while the second or proximal needle 40 may be configured to distally rotate away from the elongate member 22. Conversely, during retraction, the first needle 38 may be configured to distally rotate away from the elongate member 22, while the second needle 40 may be configured to proximally rotate toward the elongate member 22. Moreover, each of the first and second needles 38, 40 may be configured to advance and retract between respective retracted and extended positions simultaneously, or in substantially equal increments or at substantially equal rates of angular displacement. Each of the first and second needles 38, 40 may further comprise a low-profile arcuate geometry which enables the needles 38, 40 to be substantially concealed within the firing aperture 32 while in the fully retracted position, and have maximized reach during advancement. Furthermore, each arcuate needle 38, 40 may be shaped and/or otherwise configured to rotate in a cammed fashion such that advancing the needles 38, 40 through tissue creates a progressively tighter pull and an ultimately tighter fastening of the tissue.

In addition, each of the first and second needles 38, 40 of FIGS. 2 and 3 may include one or more of needle hooks 46, grooves, tines, recesses, canted surfaces, or any other suitable structure or feature configured to enable engagement with a fastener or suture 34, or one or more needle guides 48 thereof. As shown in FIGS. 2 and 3, for example, a hook 46 may be disposed on an outer edge of each of the first and second needles 38, 40 and configured to engage with a needle guide 48 of a suture 34 as the respective needle 38, 40 is retracted from the fully extended position. While the embodiments of FIGS. 2 and 3 may depict the needles 38, 40 with retrograde-type hooks 46 configured to engage a suture 34 during retraction, it will be understood that other configurations may be equally or similarly employed, such as antegrade-type hooks configured to engage a suture 34 during advancement, or the like. In still further alternatives, one or more hooks may be disposed on an inner edge of each of the needles 38, 40.

Turning now to FIGS. 4-9, more detailed drawings of the first and second needles 38, 40 are provided illustrating the relative rotational positions thereof as the needles 38, 40 are advanced from fully retracted positions to fully extended positions. As shown, each of the first and second needles 38, 40 may be operatively coupled to a drive mechanism 50 that is configured to advance the needles 38, 40 from the retracted positions to the extended positions during an engagement of the drive mechanism 50 received via the control end 24 of the suturing device 20, and conversely, to retract the needles 38, 40 from the extended positions to the retracted positions during a disengagement of the drive mechanism 50 received via the control end 24. Furthermore, the drive mechanism 50 may include a multi-bar linkage, such as a three-bar linkage, or the like, which operatively couples the control end 24 to each of the first and second needles 38, 40. While only one possible arrangement for the drive mechanism 50 is described, it will be understood that other configurations and variations of the drive mechanism 50 will be readily apparent to those of skill in the art and within the scope of the appended claims.

As shown in FIGS. 4-9, the drive mechanism 50 may include at least a first drive link 52 for driving the first needle 38 and a second drive link 54 for driving the second needle 40, each of which may be slidably disposed within the elongate member 22 and in operative communication between the control end 24 and the working end 26. The drive mechanism 50 may additionally include a first intermediate link 56 for driving the first needle 38 and a second intermediate link 58 for driving the second needle 40, each of which may configured to pivotally couple the corresponding drive link 52, 54 to the corresponding needle 38, 40. In other modifications, one or more links may be omitted or added to the drive mechanism 50. As the needles 38, 40 are oppposedly arranged, the drive links 52, 54 and the intermediate links 56, 58 may be configured to be slidably and pivotally driven in substantially equal increments or rates of displacement, but in opposing directions relative to one another. For example, during advancement, the first drive link 52 of the first needle 38 may be slidably driven distally toward the working end 26 at substantially the same rate or in similar increments as the second drive link 54 of the second needle 40 being driven proximally away from the working end 26.

Figure 4:
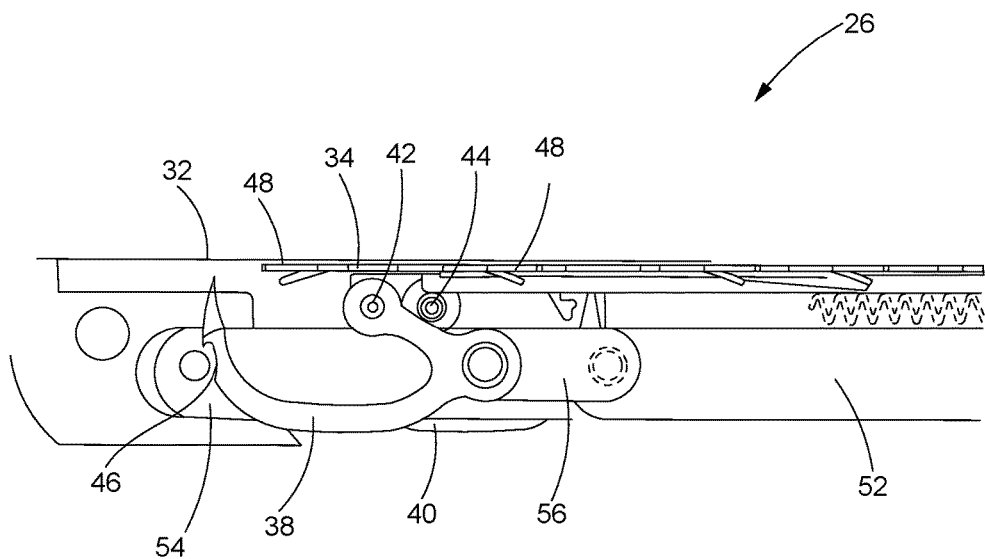
FIG. 4 is a cross-sectional side plan view of the working end of a suturing device with first and second needles disposed in the fully retracted positions.
Figure 5:
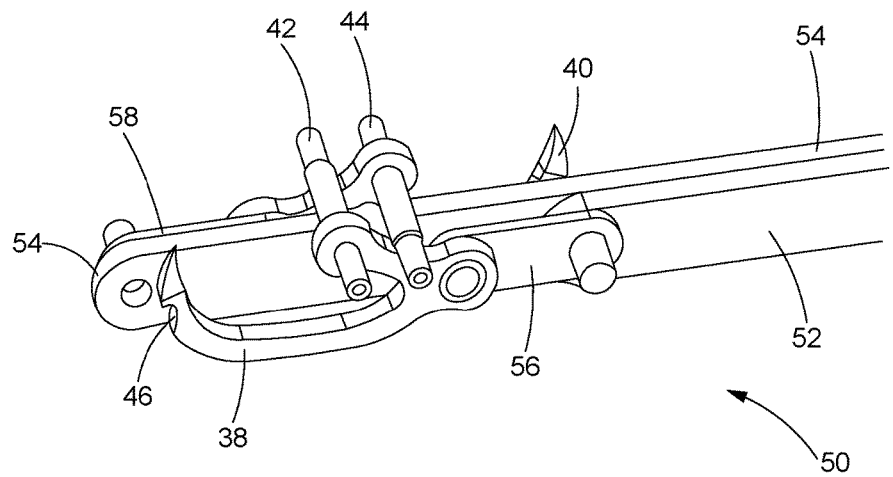
FIG. 5 is a partial perspective view of the working end of a suturing device with first and second needles disposed in the fully retracted positions.
Figure 6:
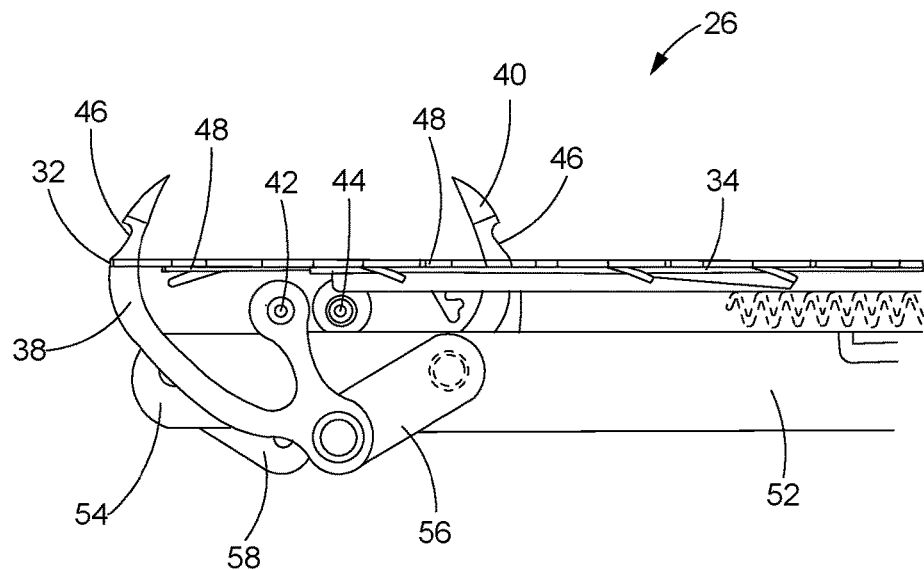
FIG. 6 is a cross-sectional side plan view of the working end of a suturing device with first and second needles disposed in partially extended positions.
Figure 7:
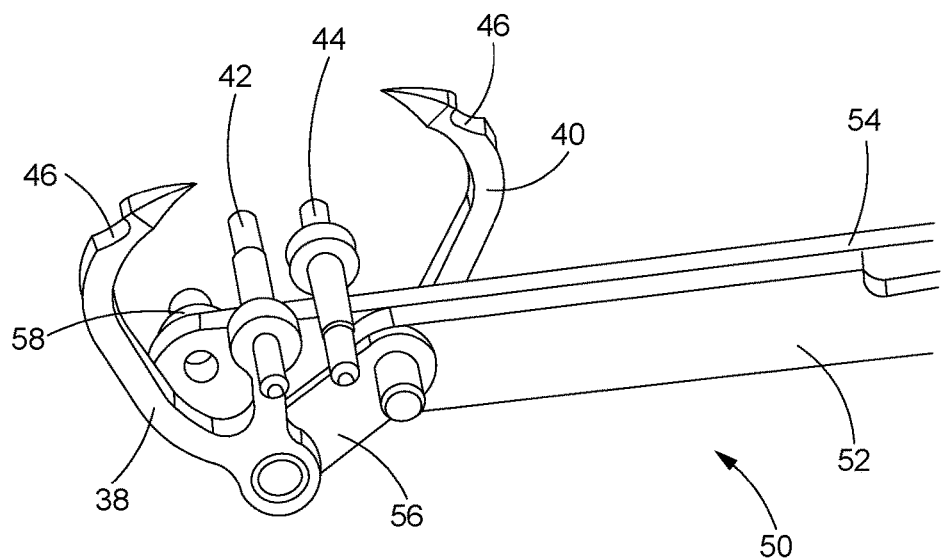
FIG. 7 is a partial perspective view of the working end of a suturing device with first and second needles disposed in partially extended positions.

In the fully retracted positions, as shown in FIGS. 4 and 5 for example, each of the first and second needles 38, 40 may be substantially concealed beneath the firing aperture 32 and within the working end 26 of the suturing device 20 so as to facilitate insertion thereof into minimal incisions or access ports, or the like. The first and second needles 38, 40 may further include a low-profile geometry which enables the working end 26 of the suturing device 20 as well as the access ports to be generally smaller in size. During advancement or during engagement of the drive mechanism 50, as shown in FIGS. 6 and 7 for example, the first drive link 52 may drive or push the first intermediate link 56 toward the distal end of the firing aperture 32 thereby causing the first needle 38 to rotate about the first fixed axis 42 and upwardly extend from the distal end of the firing aperture 32, while the second drive link 54 may drive or pull the second intermediate link 58 toward the proximal end of the firing aperture 32 thereby causing the second needle 40 to rotate about the second fixed axis 44 and upwardly extend from the proximal end of the firing aperture 32. Moreover, the drive mechanism 50 may be configured to rotatably extend the needles 38, 40 such that the reach of each needle 38, 40 is maximally extended during advancement even with a low-profile geometry so as to sufficiently penetrate tissue and/or prosthetic material to be fastened or sutured.

Figure 8:
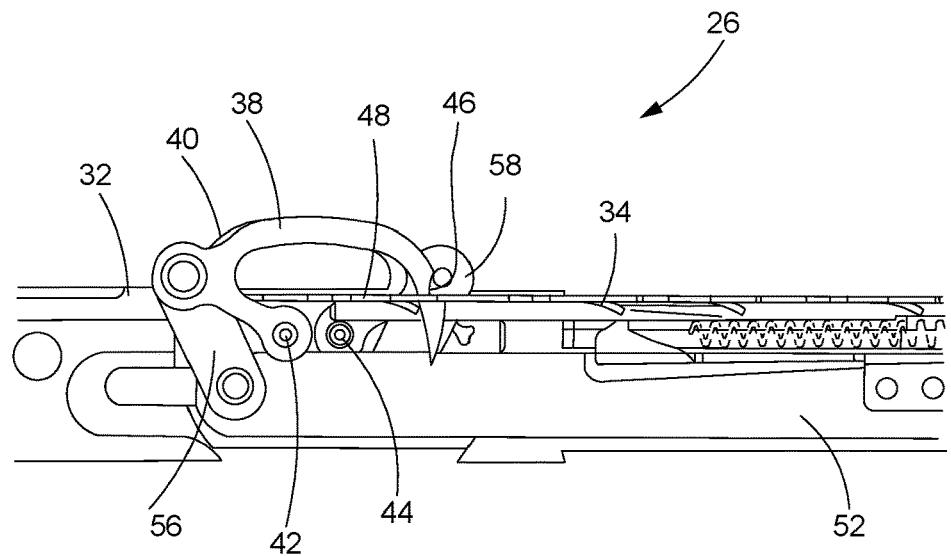
FIG. 8 is a cross-sectional side plan view of the working end of a suturing device with first and second needles disposed in fully extended positions.
Figure 9:
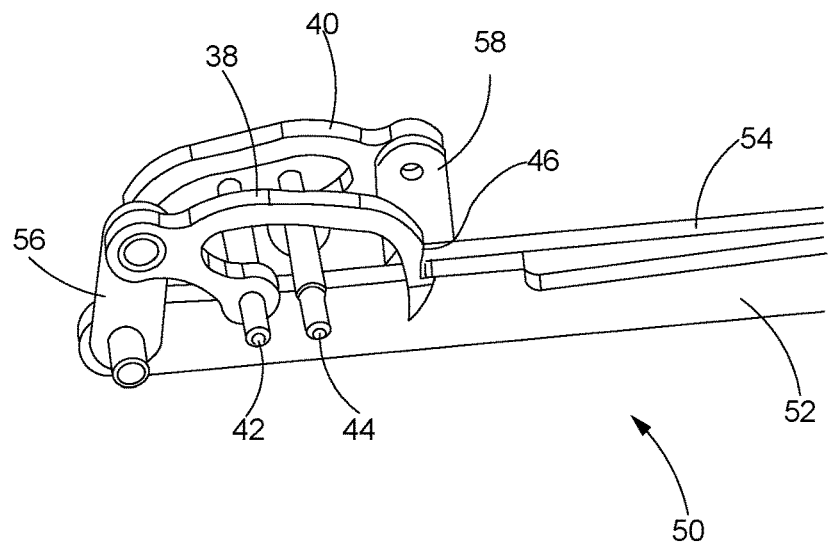
FIG. 9 is a partial perspective view of the working end of a suturing device with first and second needles disposed in fully extended positions.

The drive mechanism 50 may continue advancing each of the first and second needles 38, 40 until the needles 38, 40 respectively reach the fully extended positions, as shown for example in FIGS. 8 and 9. In particular, the drive mechanism 50 may be configured such that each of the first and second needles 38, 40 extend until at least one or more of the hooks 46 thereof engage with a fastener or suture 34 for deployment. For example, positioning of the first and second needles 38, 40, the drive mechanism 50, the firing aperture 32, and the sutures 34 may be configured such that retrograde-type hooks 46 on the outer edges of the needles 38, 40 are able to fully engage with one or more corresponding needle guides 48 of a given suture 34. In other alternatives, each of the needles 38, 40 may employ a retrograde-type hook disposed on the inner edge thereof, an antegrade-type hook disposed on the outer edge thereof, an antegrade-type hook disposed on the inner edge thereof, a retrograde-type hook disposed on a side or lateral edge thereof, an antegrade-type hook disposed on a side or lateral edge thereof, or any other suitable variation thereof, to which each of the drive mechanism 50, the firing aperture 32, and the like, may be modified to enable sufficient engagement with the corresponding needle guide 48 of a given suture 34.

Once the first and second needles 38, 40 respectively reach the fully extended positions thereof as shown for example in FIGS. 8 and 9, and once a suture 34 is fully engaged, the drive mechanism 50 may be released or disengaged, so as to retract the needles 38, 40 and deploy the engaged suture 34 within tissue and/or prosthetic material to be fastened. Moreover, the needles 38, 40 may be retracted toward the positions shown in FIGS. 4 and 5 by essentially reversing the drive mechanism 50. During retraction or during disengagement of the drive mechanism 50, for example, the first drive link 52 may drive or pull the first intermediate link 56 toward the proximal end of the firing aperture 32 thereby causing the first needle 38 to rotate in reverse about the first fixed axis 42 and downwardly retract into the distal end of the firing aperture 32. Correspondingly, the second drive link 54 may drive or push the second intermediate link 58 toward the distal end of the firing aperture 32 thereby causing the second needle 40 to rotate in reverse about the second fixed axis 44 and downwardly retract into the proximal end of the firing aperture 32. Furthermore, each of the first and second needles 38, 40 may be retracted until the needles 38, 40 return to the fully retracted positions of FIGS. 4 and 5 and until a previously engaged suture 34 is completely deployed and released therefrom, at which point the needles 38, 40 may be advanced again to engage with a new suture 34 for deployment.

While one possible implementation is provided in the drawings, other needle arrangements and/or drive mechanism configurations therefor will be apparent to those skilled in the art without departing from the scope of the appended claims. For example, in other modifications, the suturing device 20 may employ more than two needles which, for instance, partially oppose one another, or alternatively, rotate in like manner and direction relative to one another. In alternative modifications, the needles 38, 40 may be configured to be rotated sequentially rather than simultaneously relative to one another, and/or configured to be rotated at non-identical rates of angular displacement relative to one another. In additional modifications, the needles 38, 40 may be configured to rotate about a common axis rather than axially offset. In further modifications, the suturing device 20 may provide a needle that is configured to rotate about an axis that is parallel, or otherwise generally not perpendicular, to the elongate member 22. In still further modifications, the working end 26 of the suturing device 20 may be articulated, such as pivotable or otherwise movable, relative to the elongate member 22 about one or more axes.

Figure 10:
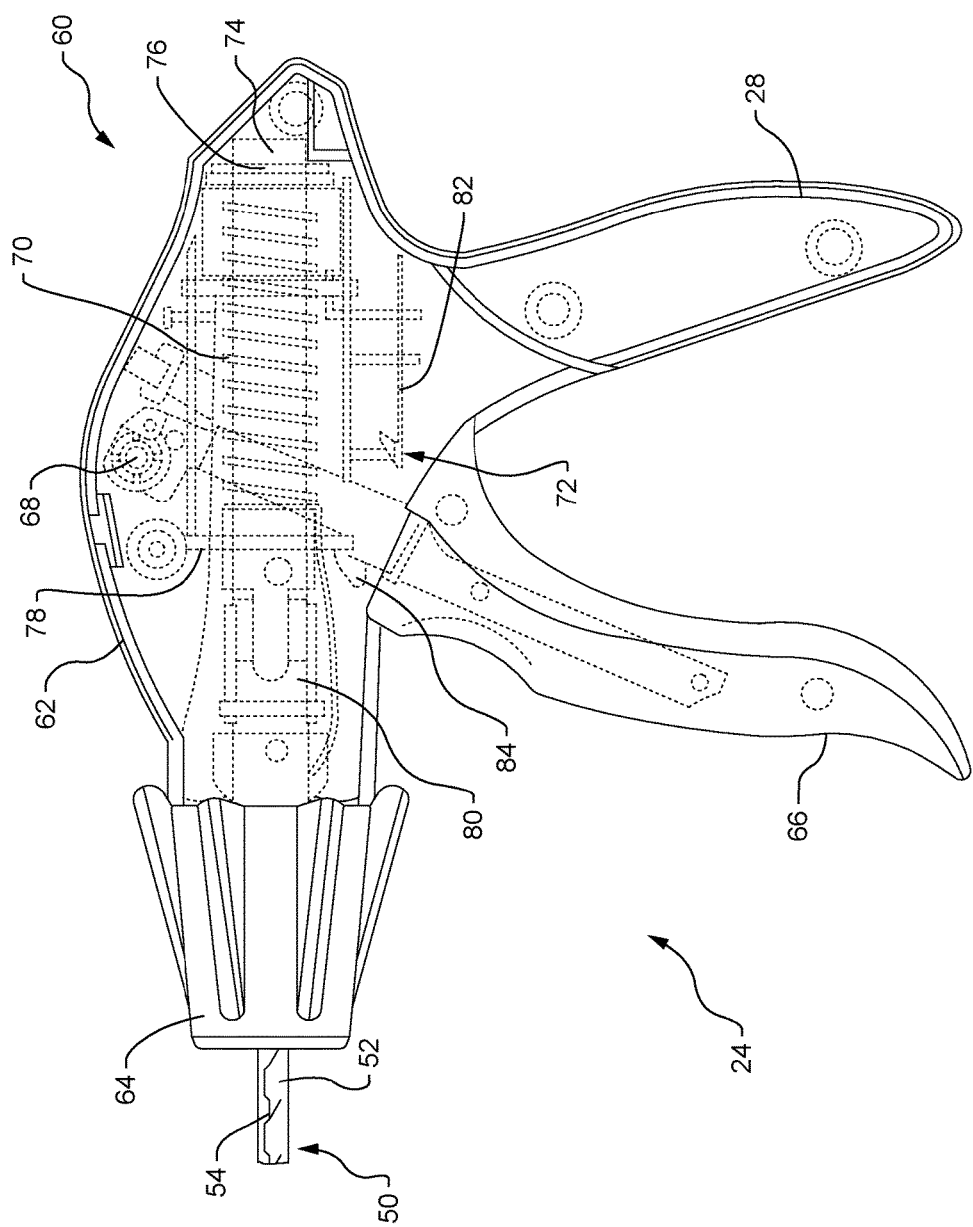
FIG. 10 is a cross-sectional side plan view of the control end and impulse mechanism of a suturing device.
Figure 11:
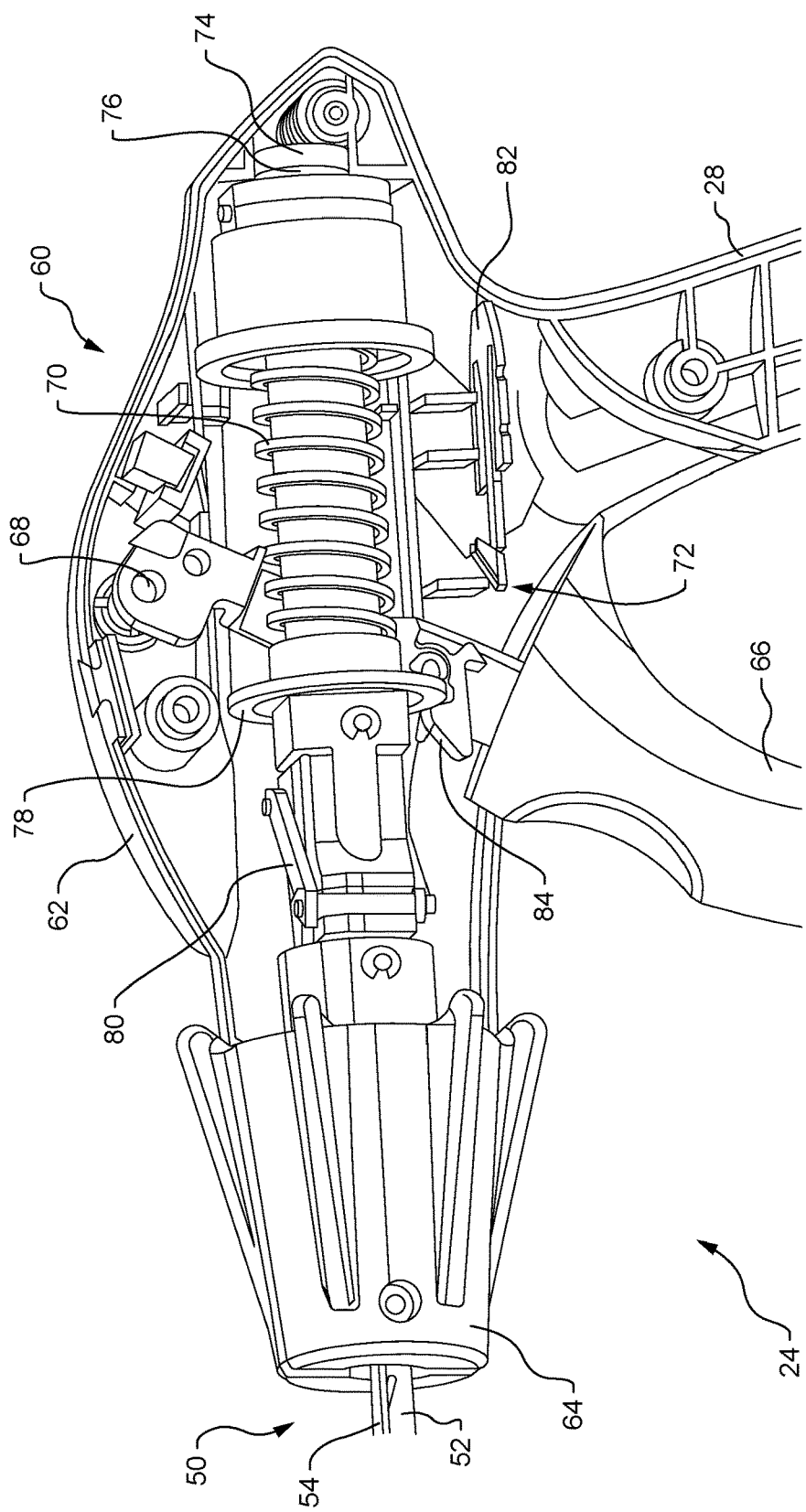
FIG. 11 is a partial perspective view of the control end and impulse mechanism of a suturing device.

The suturing device 20 may further employ a triggering mechanism with an impulse feature, or the impulse mechanism 60 shown in FIGS. 10 and 11 for example, that is operatively coupled to the drive mechanism 50 and configured to facilitate the deployment of sutures 34 into tissue. As shown, the impulse mechanism 60 may be disposed within a housing 62 provided at the control end 24 of the suturing device 20 and configured to interface with the first and second needles 38, 40 via the elongate member 22 and the drive mechanism 50 disposed therein. Furthermore, one or more of the elongate member 22 and the drive mechanism 50 therein may be rotatably coupled to the housing 62 via a rotating collar 64 which may be used to adjust the radial position of the firing aperture 32 relative to the control end 24. The housing 62 may additionally provide for the grip 28 shown, relative to which a trigger 66 of the impulse mechanism 60 may be pivotally anchored by an anchoring pin 68 and movable in either of two directions, for example, between a first or distal position that is farthest from the grip 28, and a second or proximal position that is nearest the grip 28. In general, when the trigger 66 is pulled toward the grip 28, the drive mechanism 50 may be engaged to advance the needles 38, 40, and when the trigger 66 is pushed away from the grip 28, the drive mechanism 50 may be disengaged to retract the needles 38, 40. In alternative embodiments, the trigger 66 may provide additional features, such as handles, grips, finger loops, extensions, or the like, designed to not only aid in pulling the trigger 66 toward the grip 28, but to also facilitate the ability to push the trigger 66 away from the grip 28.

Still referring to FIGS. 10 and 11, the impulse mechanism 60 may further include a tensioning device 70 and a ratchet arrangement 72, both of which operatively couple the trigger 66 to the drive mechanism 50. Moreover, the tensioning device 70 and the ratchet arrangement 72 may be configured to accumulate energy during engagement and while the suturing needles 38, 40 are advanced, and instantaneously release the accumulated energy during disengagement, or when deployment of a given suture 34 is desired, so as to facilitate the retraction of the needles 38, 40 from tissue. As shown for example in FIG. 11, the tensioning device 70 may include at least one compression spring, or at least one spring biased in the decompressed state, that is coaxially disposed along a control shaft 74 and extending between a stopper plate 76 and a slider disc 78. Furthermore, the slider disc 78 may be slidably movable along the control shaft 74 and capable of adjusting the tension or the amount of energy stored in the one or more springs of the tensioning device 70. The slider disc 78 may further be coupled to a reversing device 80 that is operatively coupled to each of the distal and proximal drive links 52, 54 of the drive mechanism 50 and configured to move the distal and proximal drive links 52, 54 and the corresponding needles 38, 40 in substantially equal increments but in opposing directions. In alternative embodiments, the tensioning device 70 and the ratchet arrangement 72 may be configured to accumulate energy during engagement and while the suturing needles 38, 40 are advanced, but instantaneously release the accumulated energy at a final stage of the engagement so as to facilitate the final insertion of the suture 34 and the needles 38, 40 into tissue.

As shown in FIGS. 10 and 11, the ratchet arrangement 72 may serve to selectively couple the trigger 66 to the tensioning device 70, and correspondingly to the drive mechanism 50. For example, the ratchet arrangement 72 may include a ratchet pawl 82 and a ratchet latch 84, collectively configured to accumulate energy in the tensioning device 70 during engagement of the needles 38, 40, and instantaneously release the accumulated energy through the drive mechanism 50 during disengagement. Specifically, the ratchet pawl 82 may be bendably coupled to the housing 62 of the control end 24, and the ratchet latch 84 may be pivotally coupled relative to the trigger 66 and caused to interface with either of the slider disc 78 or the ratchet pawl 82 depending on the position of the trigger 66. In one embodiment, the ratchet latch 84 may be configured to create a first interface between the trigger 66 and the tensioning device 70 when the trigger 66 is in the first position and while the trigger 66 is being controlled to advance the needles 38, 40 during engagement. Correspondingly, the ratchet latch 84 may be configured to create a second interface between the trigger 66 and the ratchet pawl 82 when the trigger 66 is in the second position and while the trigger 66 is being controlled to retract the needles 38, 40 during disengagement. The ratchet latch 84 may further employ one or more springs or other comparable means to bias the ratchet latch 84 in an orientation which favors the first interface with the slider disc 78 rather than the second interface with the ratchet pawl 82.

Figure 12:
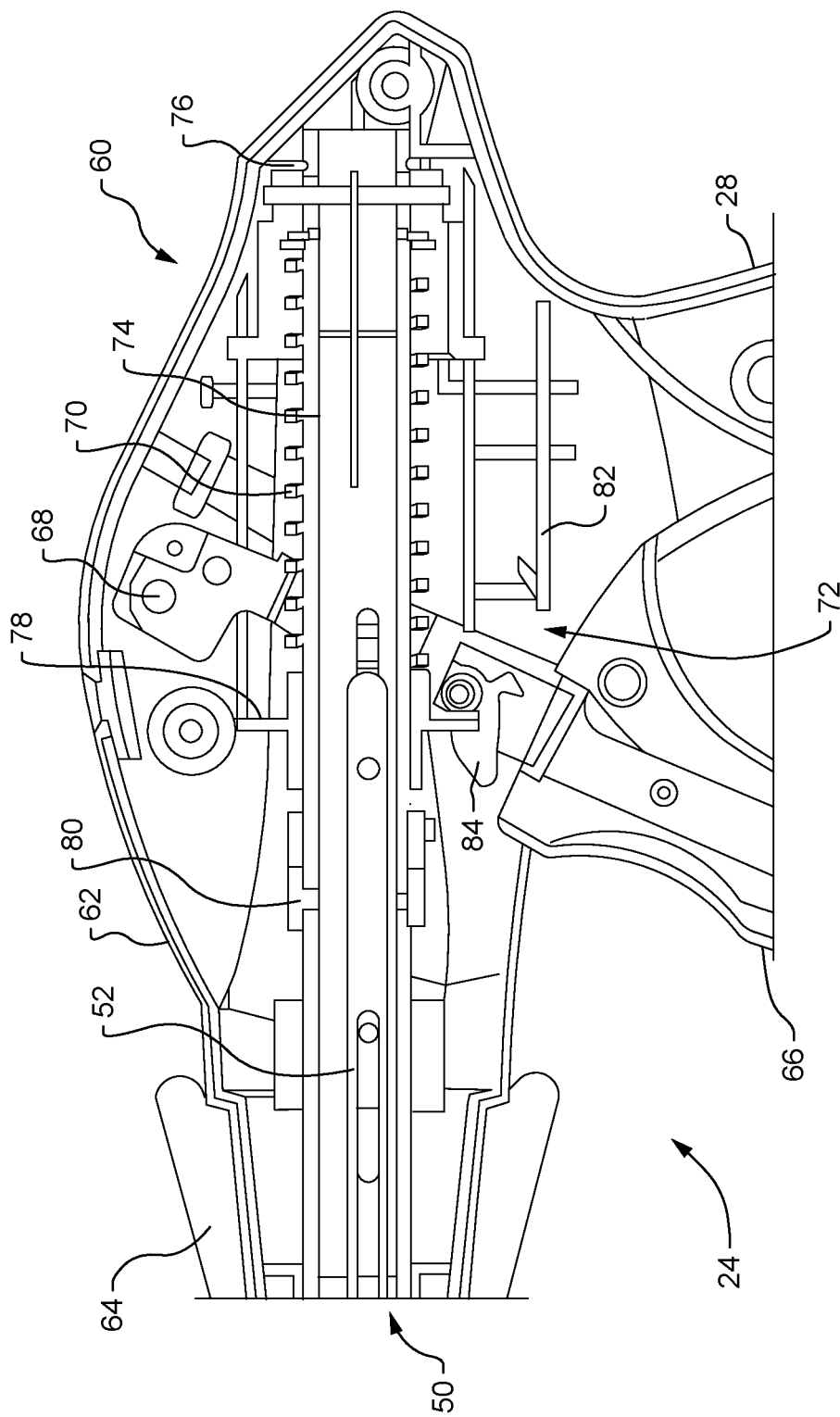
FIG. 12 is a cross-sectional side plan view of the control end and impulse mechanism of a suturing device in a default state.
Figure 13:
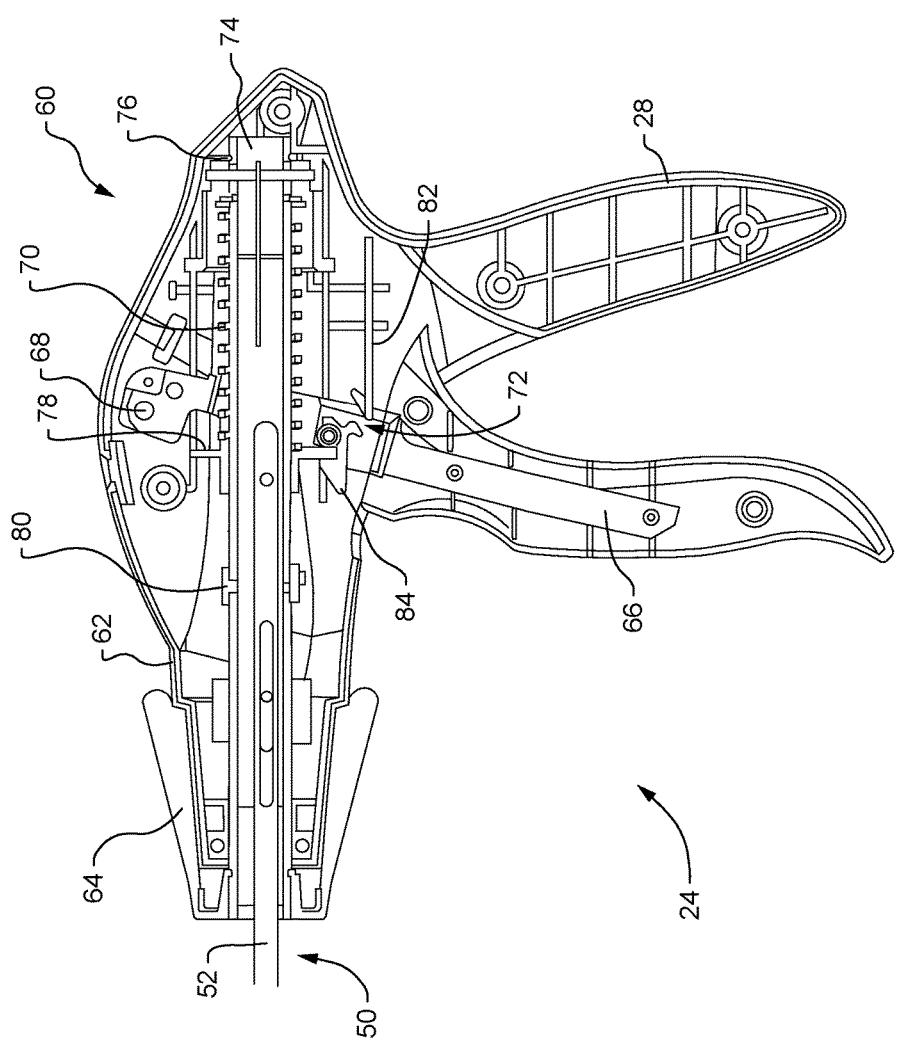
FIG. 13 is a cross-sectional side plan view of the control end and impulse mechanism of a suturing device in a partially engaged state.
Figure 14:
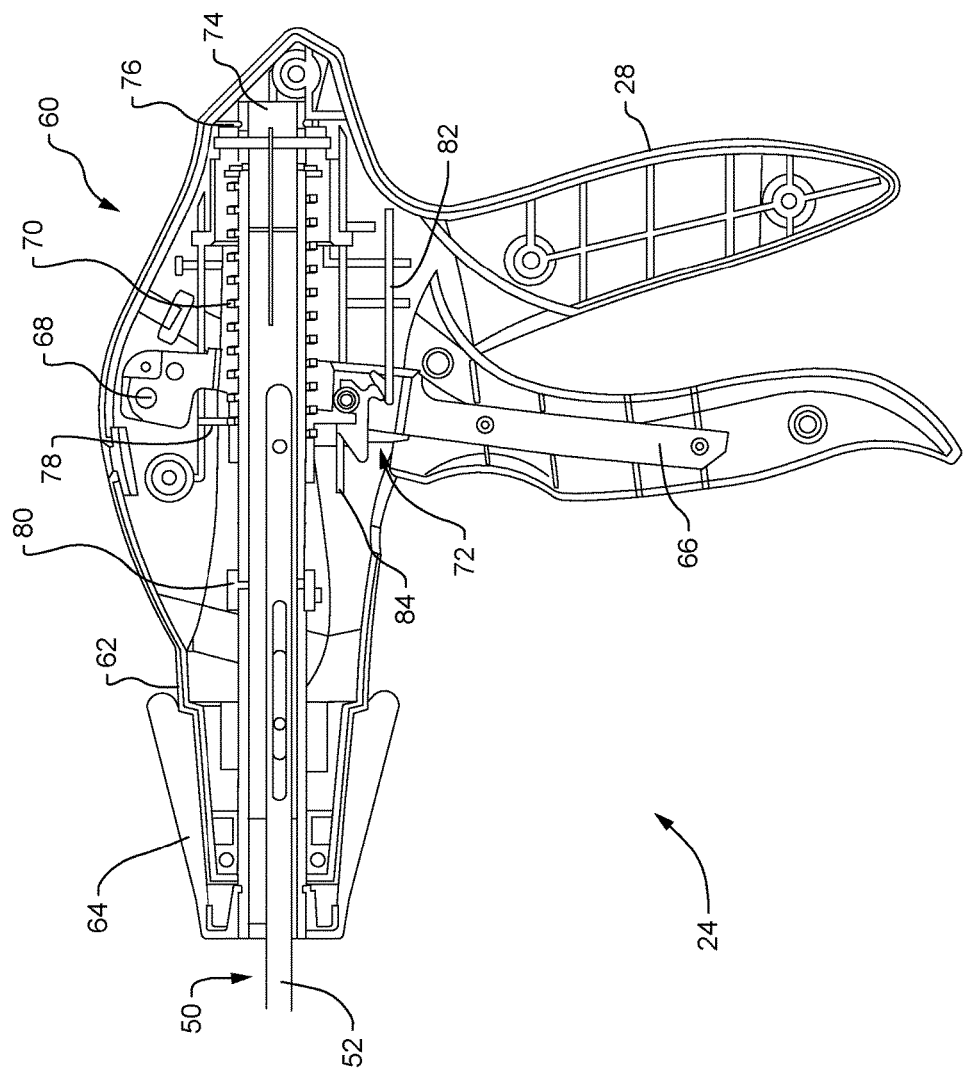
FIG. 14 is a cross-sectional side plan view of the control end and impulse mechanism of a suturing device in another partially engaged state.
Figure 15:
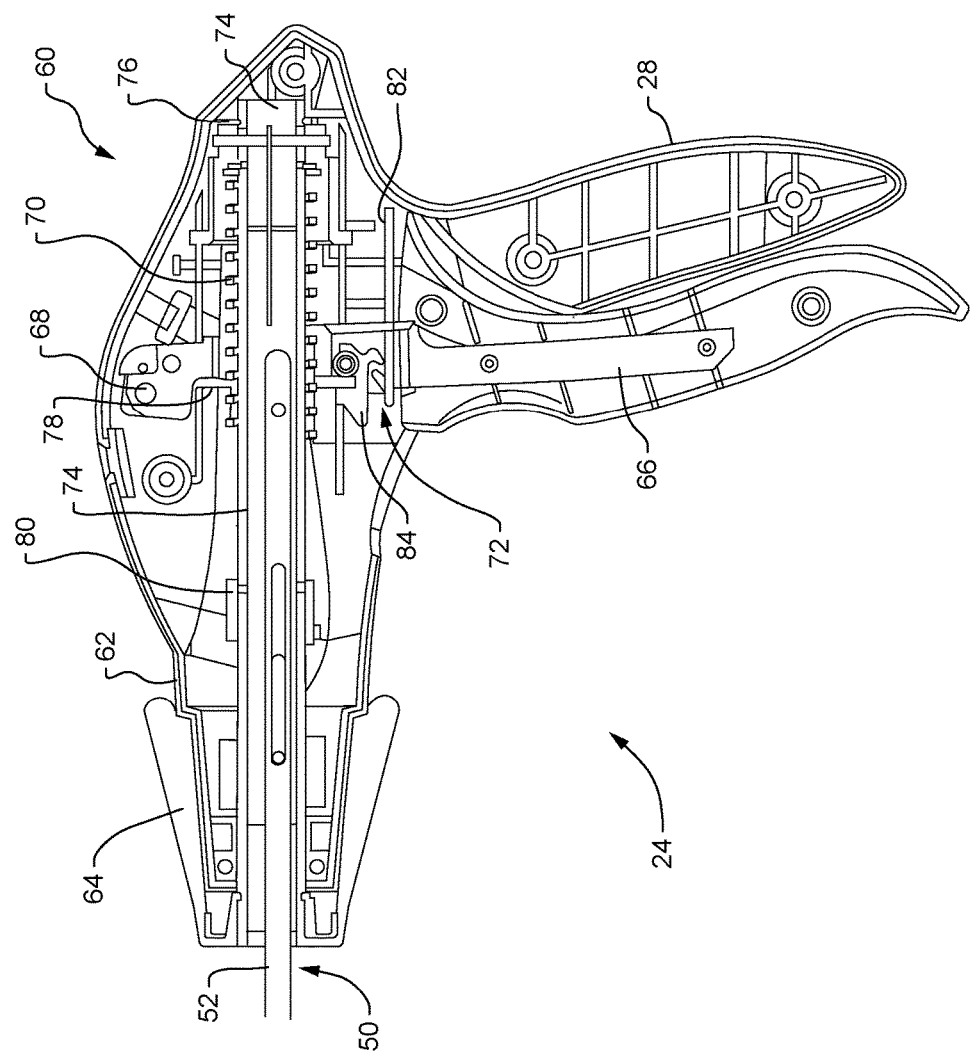
FIG. 15 is a cross-sectional side plan view of the control end and impulse mechanism of a suturing device in a fully engaged state.

Turning to FIGS. 12-19, one exemplary means by which the impulse mechanism 60 may operate during engagement and disengagement is provided. As shown in the initial default state of FIG. 12, the trigger 66 may be disposed in the first position farthest from the grip 28, and the drive mechanism 50 as well as the corresponding needles 38, 40 may be completely disengaged. Furthermore, the tensioning device 70 in FIG. 12 is uncompressed and remains at rest, while the ratchet latch 84 forms the first interlocking interface with the slider disc 78. As the trigger 66 is pulled away from the first position and toward the second position nearest the grip 28 during engagement, as shown for example in FIG. 13, the ratchet latch 84 causes the slider disc 78 to not only move the drive links 52, 54 and advance the needles 38, 40, but also compress the tensioning device 70 and accumulate energy therein. As the trigger 66 is pulled closer toward the grip 28, and as the needles 38, 40 continue to advance, the tensioning device 70 continues to accumulate more energy and the ratchet latch 84 begins to interact with the ratchet pawl 82 as shown in FIG. 14. Continuing to pull the trigger 66 further toward the grip 28 may cause the ratchet latch 84 to move past the ratchet pawl 82, while slightly bending the ratchet pawl 82 downward, and into a position enabling the second interlocking interface between the ratchet latch 84 and the ratchet pawl 82 as shown in FIG. 15. Moreover, the position of the trigger 66 shown in FIG. 15 further corresponds to the fully extended state of each of the needles 38, 40, as well as the fully compressed state of the tensioning device 70.

Figure 16:
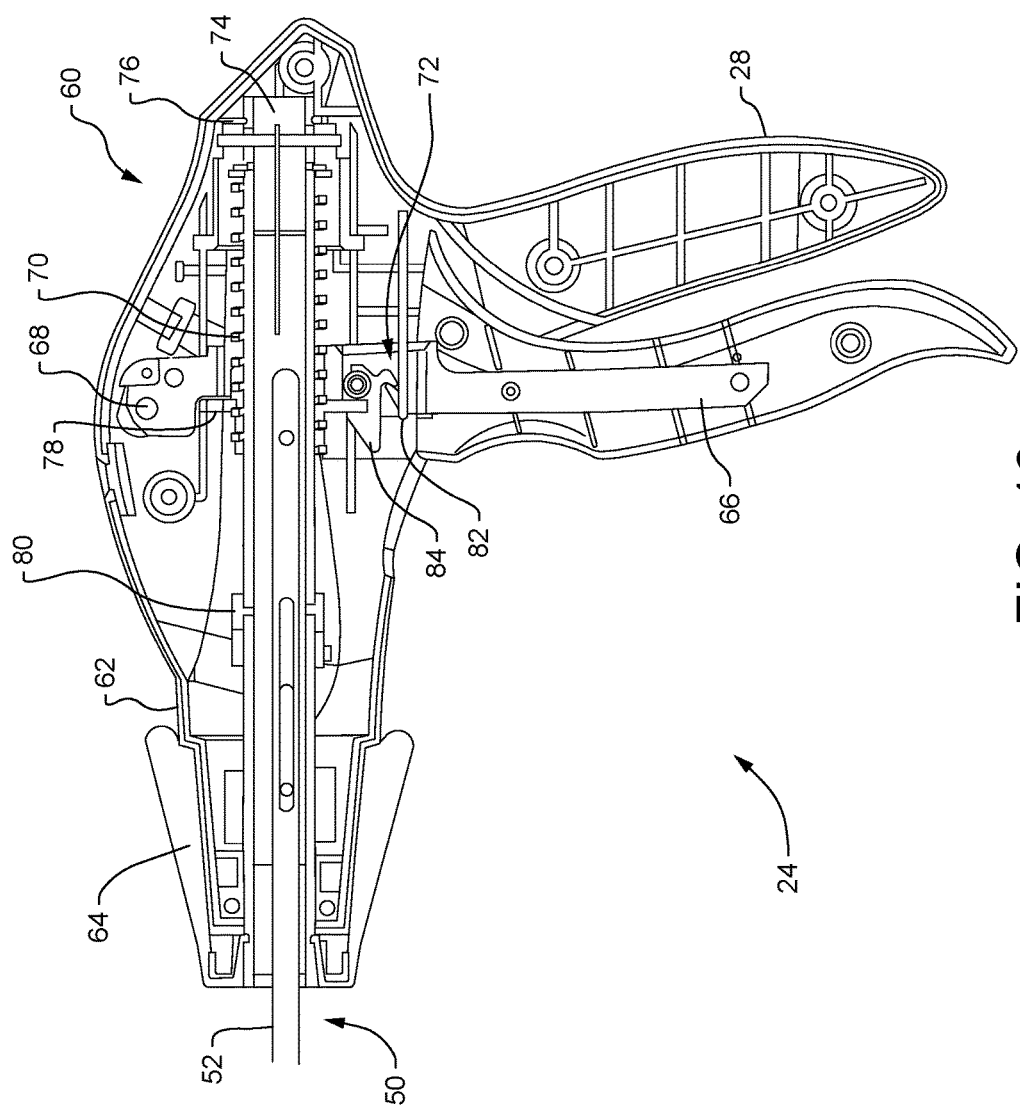
FIG. 16 is a cross-sectional side plan view of the control end and impulse mechanism of a suturing device in a partially disengaged state.
Figure 17:
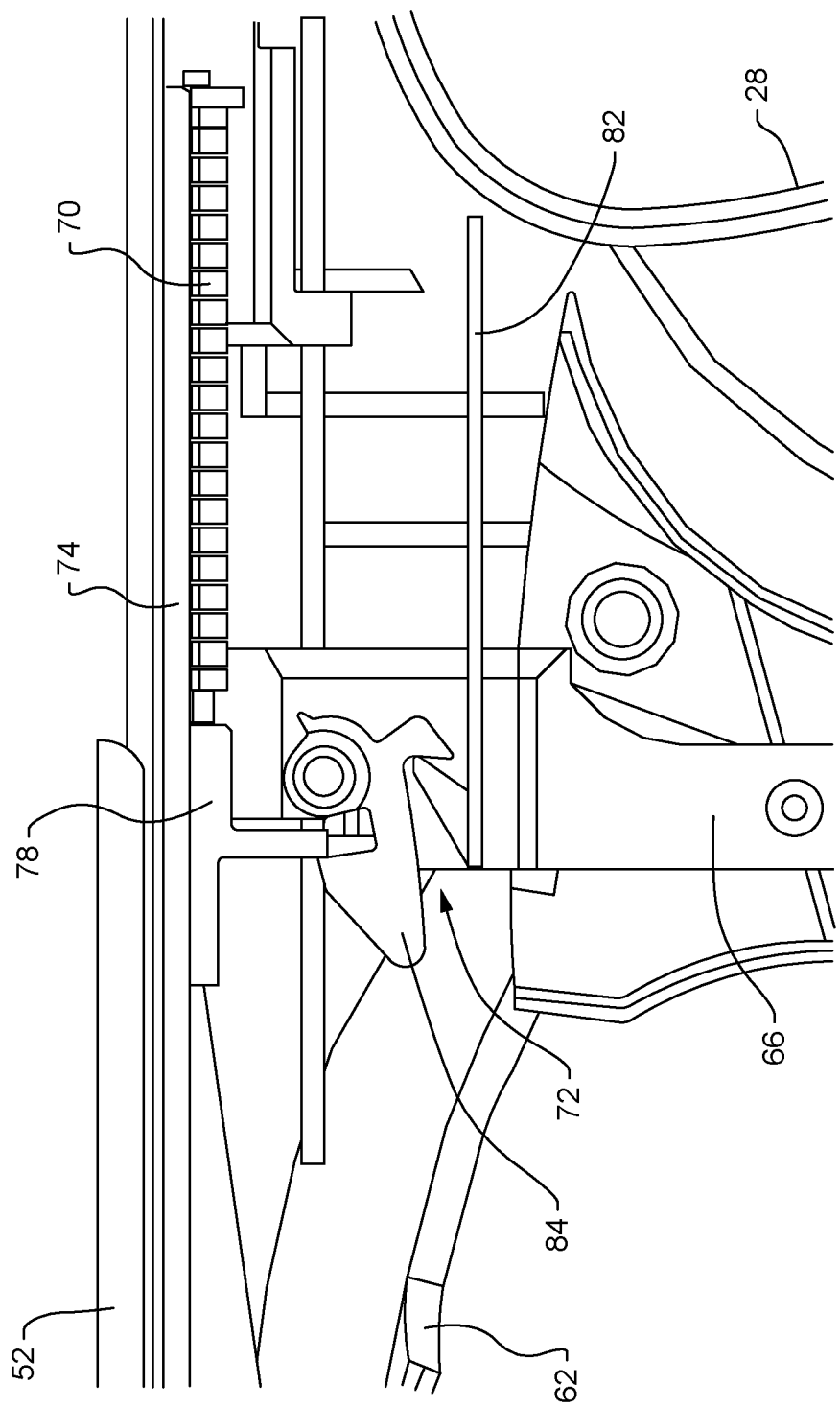
FIG. 17 is a cross-sectional side plan view of the control end and ratchet arrangement of a suturing device in another partially disengaged state.
Figure 18:
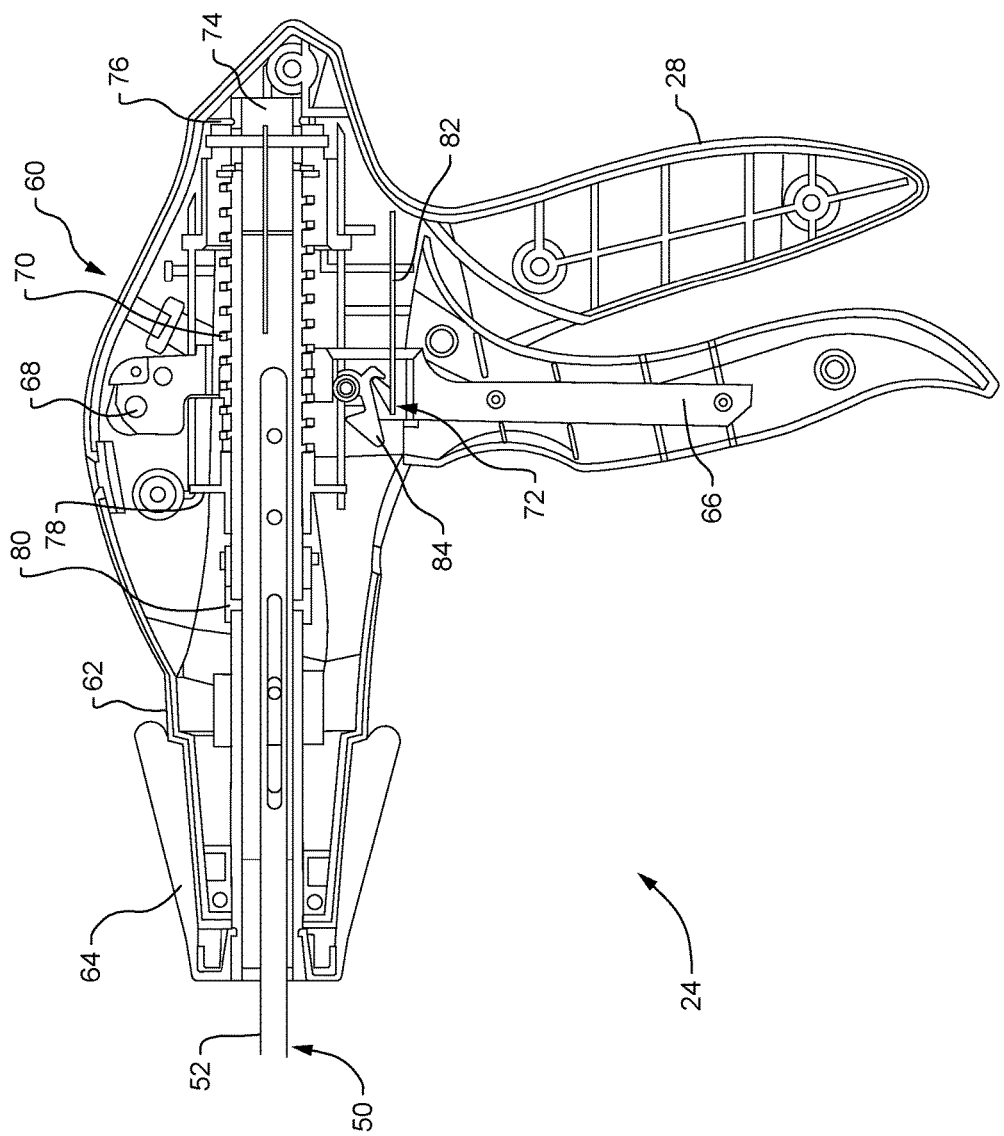
FIG. 18 is a cross-sectional side plan view of the control end and impulse mechanism of a suturing device in a fully disengaged state.

As the trigger 66 is being released to disengage or retract the needles 38, 40, the ratchet latch 84 begins to form the second interlocking interface with the ratchet pawl 82, as shown in FIGS. 16 and 17. More particularly, each of the ratchet latch 84 and the ratchet pawl 82 may be shaped and configured such that the second interlocking interface therebetween can only form during disengagement of the needles 38, 40, or when the trigger 66 is being distally moved or pushed away from the grip 28. Furthermore, the ratchet latch 84 may be configured such that the ratchet pawl 82 and the second interlocking interface therewith causes the ratchet latch 84 to pivot downward or otherwise away from the slider disc 78 as shown in FIG. 17 until the first interlocking interface with the slider disc 78 is completely removed. Once the ratchet latch 84 releases the slider disc 78 as shown in FIG. 18, the energy accumulated within the tensioning device 70 may also be released, thereby causing the drive mechanism 50 to instantaneously disengage or retract the needles 38, 40 from tissue. Moreover, releasing the accumulated energy may cause the tensioning device 70 to push the slider disc 78 toward the reversing device 80, and in turn, actuate the drive links 52, 54 of the drive mechanism 50 to instantaneously retract the needles 38, 40 and deploy a suture 34 installed in tissue.

Figure 19:
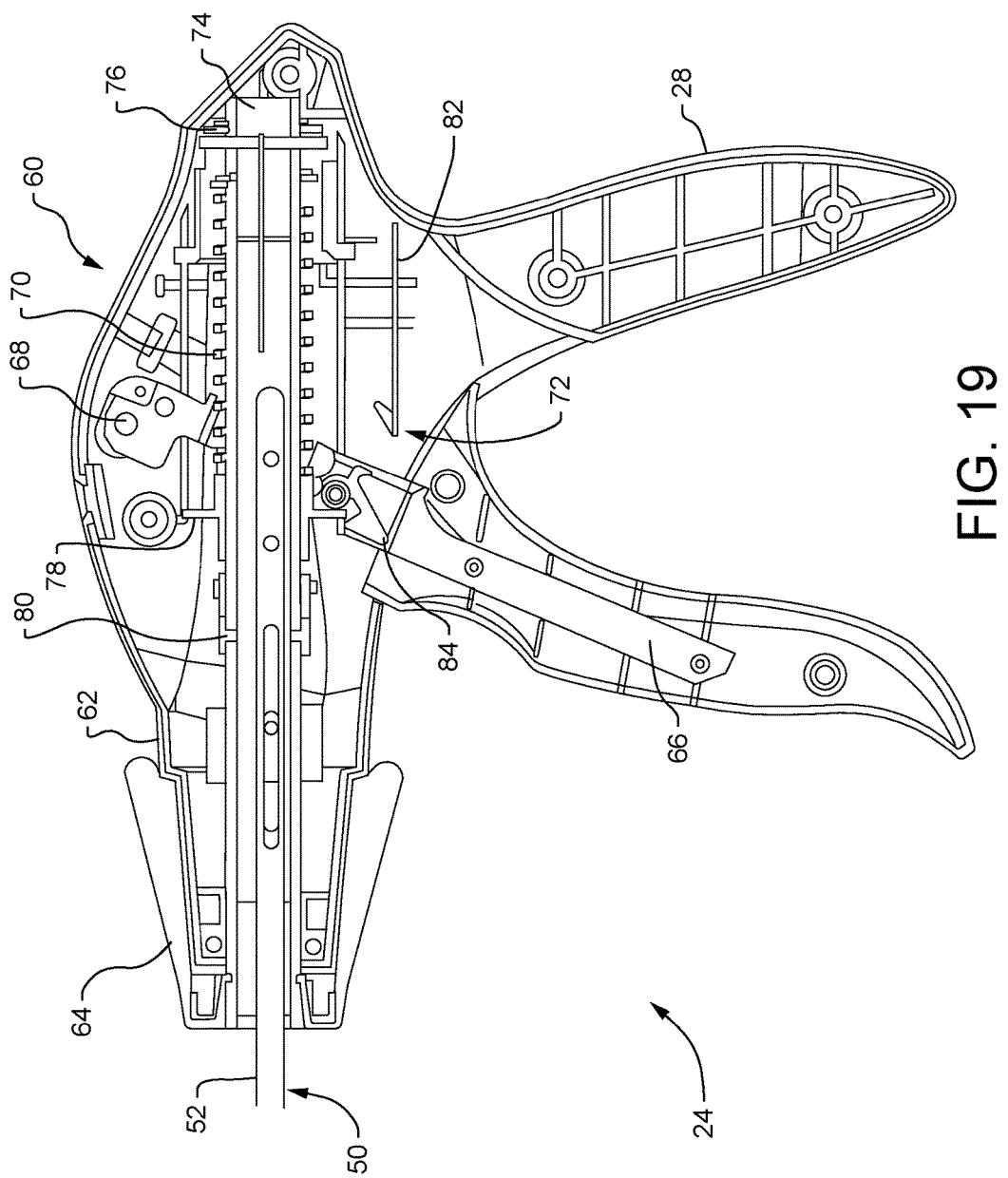
FIG. 19 is a cross-sectional side plan view of the control end and impulse mechanism of a suturing device resetting to the default state.

After a suture 34 is installed, the trigger 66 may be returned to the default or first position, which in turn, may release the ratchet latch 84 from the ratchet pawl 82 and return the ratchet latch 84 to slider disc 78 so as to reset the interlocked state therewith, as shown in FIG. 19. While the trigger 66 may be returned to the default or first position manually by hand, the trigger 66 may also be provided with biasing means, such as a spring, or the like, to automatically return the trigger 66 to the first position. In other modifications, the trigger 66 and/or the impulse mechanism 60 may be provided with a switching feature which, if desired by the user, selectively disables the impulse mechanism 60 and allows manual disengagement of the needles 38, 40 without the impulse assist. In still further modifications, the trigger 66 and/or the impulse mechanism 60 may be provided with a manual release feature which enables any energy already accumulated within the tensioning device 70 to be reset or released without fully disengaging the needles 38, 40. Furthermore, although the disclosed tensioning device 70 is a mechanical device adapted to store and release mechanical energy, other types of devices or mechanisms, such as electrically actuated devices, electro-mechanical devices, electro-hydraulic devices, pneumatic devices, and the like, may also be employed to accumulate and release other forms of potential energy and to ultimately provide comparable results.

From the foregoing, it can be seen that the present disclosure sets forth a medical fastening or suturing device adapted to rapidly and reliably install fasteners or sutures to secure tissue and/or any applicable prosthetic material. The device not only greatly reduces the time required for fastening tissues, but also results in improved ease of use relative to other methods. Furthermore, through the unique combination of elements set forth in the present disclosure, the tissue fastening or suturing is more reliably retained with reduced irritation and other complications to the patient and without adversely affecting the integrity of the attachment and/or closure.

What is claimed is:

1. A suturing device, comprising:
   at least one suturing needle;
   a drive mechanism operatively coupled to the suturing needle and configured to advance the suturing needle from a retracted position to an extended position during engagement, and retract the suturing needle from the extended position to the retracted position during disengagement; and an impulse mechanism operatively coupled to the drive mechanism and configured to accumulate energy during engagement of the suturing needle, and instantaneously release the accumulated energy through the drive mechanism during deployment;

wherein the impulse mechanism includes at least a trigger, a tensioning device and a ratchet arrangement, the ratchet arrangement being configured to couple the trigger to the tensioning device so as to accumulate energy in the tensioning device during engagement, and decouple the trigger from the tensioning device so as to instantaneously release the accumulated energy through the drive mechanism during disengagement.

2. The suturing device of claim 1, wherein the impulse mechanism includes a manual release feature to release the accumulated energy without fully disengaging the needles.

3. The suturing device of claim 1, wherein the suturing needle is rotatably disposed relative to the drive mechanism, the suturing needle having an arcuate geometry providing a low-profile in the retracted position and maximized reach during advancement, and a feature configured to engage a suture for deployment.

4. The suturing device of claim 1, further including a second suturing needle, the first and second suturing needles being rotatably configured to engage a suture for deployment, the drive mechanism being configured to advance and retract each of the first and second suturing needles in substantially equal increments but in opposing directions.

5. The suturing device of claim 1, wherein the trigger is pivotally movable from a first position to a second position during engagement and from the second position to the first position during disengagement, the trigger being biased in the first position.

6. The suturing device of claim 5, wherein the ratchet arrangement includes at least a ratchet latch pivotally coupled to the trigger and a ratchet pawl disposed at the second position, the ratchet latch being configured to create a first interface between the trigger and the tensioning device at the first position and during engagement, and create a second interface between the trigger and the ratchet pawl at the second position and during disengagement, the second interface releasing the first interface.

7. A suturing device, comprising:
an elongate member extending between a working end and a control end, the working end having a distal needle and a proximal needle disposed therein;
a drive mechanism disposed within the elongate member and operatively coupled to each of the distal and proximal needles, the drive mechanism being configured to advance each of the distal and proximal needles from a retracted position to an extended position during engagement, and retract each of the distal and proximal needles from the extended position to the retracted position during disengagement; and an impulse mechanism disposed within the control end and operatively coupled to the drive mechanism in a manner configured to selectively engage and disengage each of the distal and proximal needles, the impulse mechanism having at least a trigger, a tensioning device and a ratchet arrangement and being configured to accumulate energy during engagement, and decouple the trigger from the tensioning device so as to instantaneously release the accumulated energy through the drive mechanism during deployment.

8. The suturing device of claim 7, wherein the impulse mechanism is configured to instantaneously release the accumulated energy through the drive mechanism during disengagement.

9. The suturing device of claim 7, wherein each of the distal and proximal needles is rotatably disposed within the working end, each of the distal and proximal needles having an arcuate geometry providing a low-profile in the retracted position and maximized reach during advancement, and a feature configured to engage a suture for deployment.

10. The suturing device of claim 9, wherein the drive mechanism is configured to advance and retract each of the distal and proximal needles in substantially equal increments but in opposing directions.

11. The suturing device of claim 7, wherein the tensioning device is configured to communicate with the drive mechanism, the ratchet arrangement being configured to couple the trigger to the tensioning device so as to accumulate energy in the tensioning device during engagement, and decouple the trigger from the tensioning device so as to instantaneously release the accumulated energy through the drive mechanism during disengagement.

12. The suturing device of claim 7, wherein the tensioning device includes at least one compression spring configured to communicate with the drive mechanism.

13. The suturing device of claim 7, wherein the control end includes a grip, the trigger being pivotally movable relative to the grip from a first position to a second position during engagement and from the second position to the first position during disengagement, the trigger being biased in the first position.

14. The suturing device of claim 13, wherein the tensioning device is configured to communicate with the drive mechanism, the ratchet arrangement including at least a ratchet latch pivotally coupled to the trigger and a ratchet pawl disposed at the second position, the ratchet latch being configured to create a first interface between the trigger and the tensioning device at the first position and during engagement, and create a second interface between the trigger and the ratchet pawl at the second position and during disengagement, the second interface releasing the first interface.

15. A suturing device, comprising:
an elongate member extending between a working end and a control end and having a track for receiving one or more deployable sutures therein, the working end having a firing aperture disposed in communication with the track and a distal needle and a proximal needle rotatably disposed therein;
a drive mechanism disposed within the elongate member and including at least a distal drive link operatively coupled to the distal needle and a proximal drive link operatively coupled to the proximal needle, the drive mechanism being configured to advance each of the distal and proximal needles from a retracted position to an extended position during engagement, and retract each of the distal and proximal needles from the extended position to the retracted position during disengagement; and
an impulse mechanism disposed within the control end and operatively coupled to the drive mechanism, the impulse mechanism having at least a trigger, a tensioning device, a ratchet latch and a ratchet pawl and being configured to couple the trigger to the drive mechanism and accumulate energy in the tensioning device during engagement, and decouple the trigger from the drive mechanism and instantaneously release the accumulated energy through the drive mechanism during deployment.

16. The suturing device of claim 15, wherein the impulse mechanism is configured to instantaneously release the accumulated energy through the drive mechanism during disengagement.

17. The suturing device of claim 15, wherein the control end includes a grip, the trigger being pivotally movable relative to the grip from a first position to a second position during engagement and from the second position to the first position during disengagement, the trigger being biased in the first position, the ratchet latch being configured to create a first interface between the trigger and the tensioning device at the first position and during engagement, and create a second interface between the trigger and the ratchet pawl at the second position and during disengagement.

18. The suturing device of claim 15, wherein the ratchet latch is pivotally coupled to the trigger and biased in an orientation favoring the first interface.

19. The suturing device of claim 15, wherein the ratchet latch is configured such that the second interface automatically releases the first interface between the trigger and the tensioning device.

20. The suturing device of claim 15, wherein the ratchet latch is provided with a manual release mechanism capable of manually releasing the first interface between the trigger and the tensioning device at any point during engagement.

21. The suturing device of claim 15, wherein the impulse mechanism further includes a control shaft disposed within the control end, the tensioning device including at least one compression spring coaxially disposed along the control shaft and extending between a stopper plate and a slider disc, the slider disc being slidably disposed along the control shaft and communicating with the trigger through the ratchet latch.

22. The suturing device of claim 21, wherein the control end includes at least a reversing device coupling the distal and proximal drive links to the trigger through the slider disc and the ratchet latch, the reversing device being configured to move the distal and proximal drive links and the corresponding distal and proximal needles in substantially equal increments but in opposing, directions, each of the reversing device, the drive mechanism and the elongate member being freely rotatable relative to the control end.

* * * * *